United States Patent [19]

Dabrah et al.

[11] Patent Number: 5,087,567
[45] Date of Patent: Feb. 11, 1992

[54] ANTITUMOR ANTIBIOTIC BMY-42428

[75] Inventors: Thomas T. Dabrah, Wallingford; Grace A. Hesler, Branford; Sandra J. Hofstead, Middletown; Kin S. Lam, Cheshire; Jacqueline M. Mattei, Branford; Daniel R. Schroeder, Cromwell, all of Conn.; Koji Tomita, Tokyo, Japan

[73] Assignee: Bristol-Myers Squibb Company, New York, N.Y.

[21] Appl. No.: 464,046

[22] Filed: Jan. 12, 1990

[51] Int. Cl.$^5$ .............. C12P 01/06; C12P 17/16; C07G 03/00; C07G 11/00

[52] U.S. Cl. .............. 435/169; 435/118; 435/123; 435/125; 435/252.1; 435/825; 536/4.1; 536/16.8; 514/23; 514/183; 424/116; 424/123

[58] Field of Search .............. 424/116, 123; 435/169, 435/123, 118, 125, 825, 252.1; 536/4.1, 16.8; 514/23, 183

[56] References Cited

U.S. PATENT DOCUMENTS

| | | | |
|---|---|---|---|
| 4,277,478 | 7/1981 | Zahner et al. | 435/119 |
| 4,551,533 | 11/1985 | Lee et al. | 435/118 |
| 4,578,468 | 3/1986 | Carter et al. | 435/118 |
| 4,774,184 | 9/1988 | Lee et al. | 435/118 |
| 4,859,598 | 8/1989 | Carter et al. | 435/119 |

OTHER PUBLICATIONS

Bergey's Manual of Systematic Bacteriology, vol. 2, pp. 1458-1459.
Gherna et al., ATCC Catalogue of Bacteria and Phages, 17th Ed., 1989, pp. 8 and 239-241.
Shirling et al., Int. J. Syst. Bact., vol. 22(4), 1972, pp. 265-394.
Kobayashi et al., The Journal of antibiotics, XLI, No. 6, p. 741 (1988), "Actinoplanones C, D, E, F and G".
Nakagawa et al., The Journal of Antibiotics, XL, No. 3, p. 301 (1987), "Structure of Cervinomycin, a Novel Xantone Antibiotic Active Against Anaerobe and Mycoplasm".
Onoprienko et al., Bioorg. Khim., 10, No. 4, p. 1418 (1978), "The Chemistry of Albofungin".

Primary Examiner—Johnnie R. Brown
Assistant Examiner—Pamela S. Webber
Attorney, Agent, or Firm—David M. Morse; William T. Han

[57] ABSTRACT

An antitumor antibiotic designated BMY-42428 is produced by fermentation of Actinomadura madurae ATCC-53806. The BMY-42428 antibiotic exhibits both antimicrobial and antitumor activities.

6 Claims, 4 Drawing Sheets

ANTITUMOR ANTIBIOTIC BMY-42428

1. Field of the Invention

This invention is directed to a new antitumor antibiotic designated herein as BMY-42428 and to a process for the preparation, isolation and purification of BMY-42428.

2. Description of the Prior Art

Although the complete structure of BMY-42428 has not yet been ascertained, the compound has been obtained in substantially pure form and characterized by physical, chemical and biological properties. No compound having the characteristics of BMY-42428 is known by the present inventors.

SUMMARY OF THE INVENTION

This invention relates to a novel antitumor antibiotic designated BMY-42428 and to a fermentation process for preparation of BMY-42428 using a new strain of *Actinomadura madurae* (ATCC-53806). This invention also relates to the new microorganism employed in the fermentative production of BMY-42428 and to the use of BMY-42428 as an antimicrobial agent and an antitumor agent.

DETAILED DESCRIPTION OF THE INVENTION

The Microorganism

Figure 1:
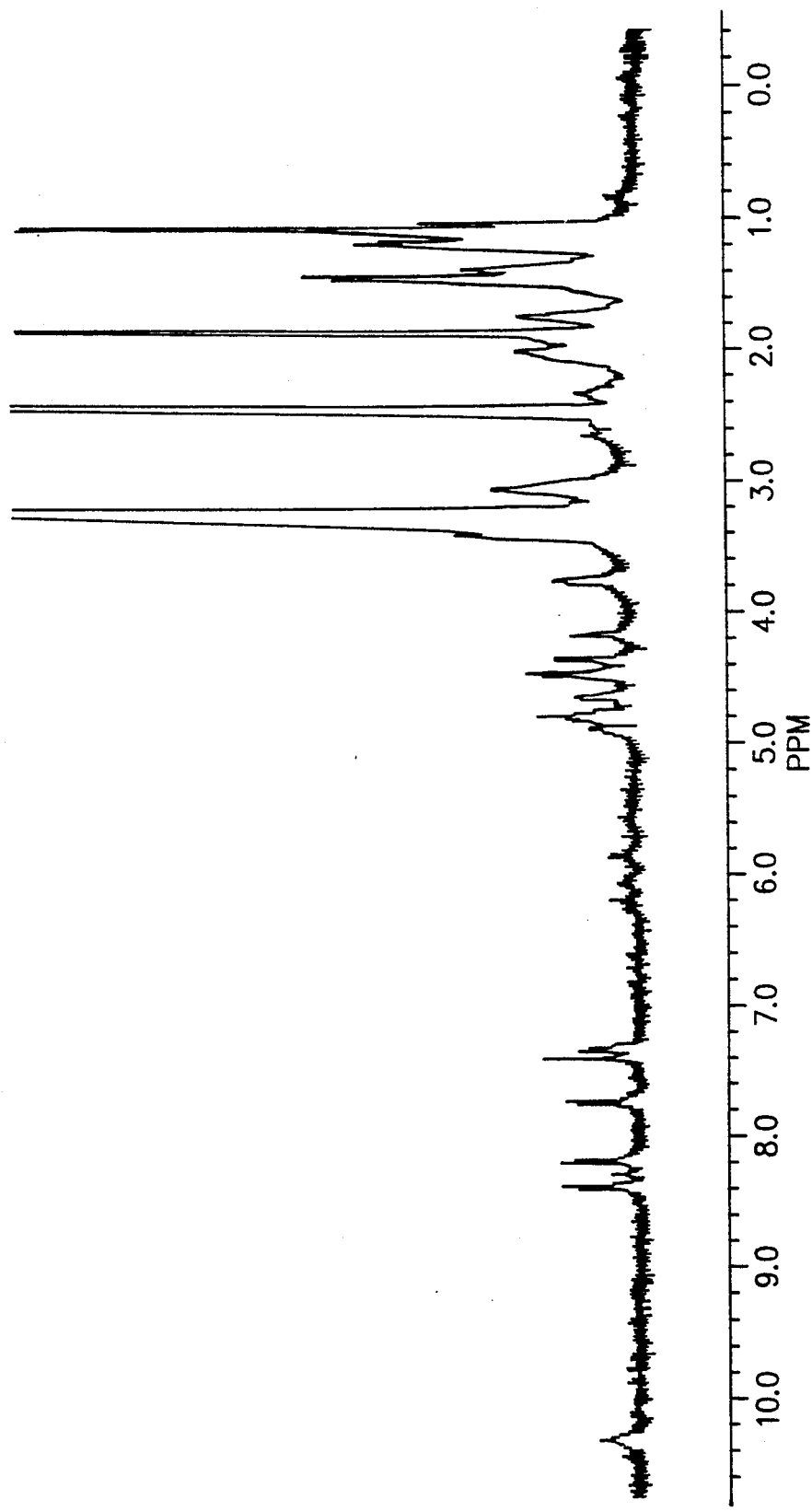
FIG. 1 is an NMR spectrum of BMY-42428 in DMSO.
Figure 2:
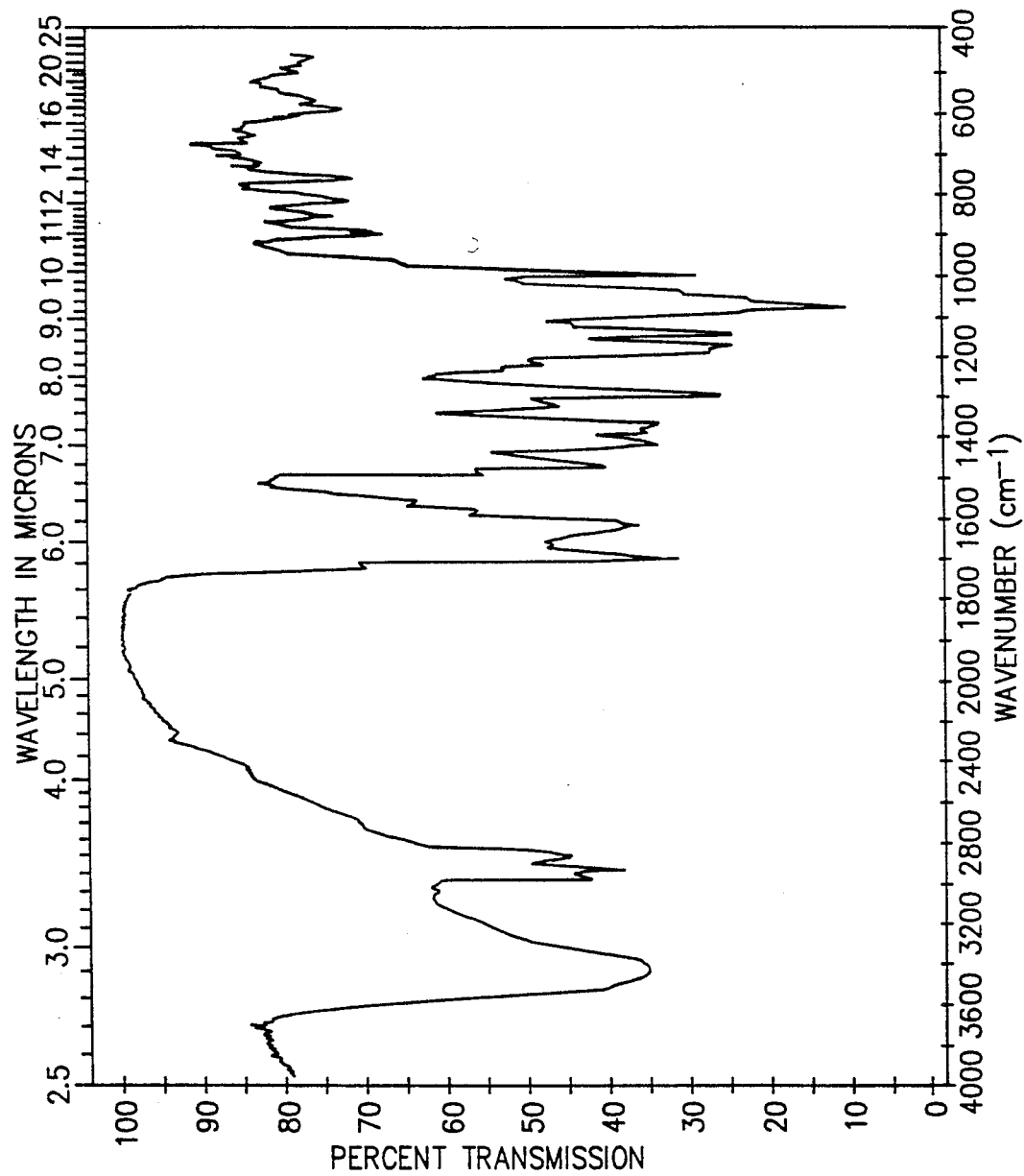
FIG. 2 is an IR spectrum of BMY-42428 in KBr pellet.
Figure 3:
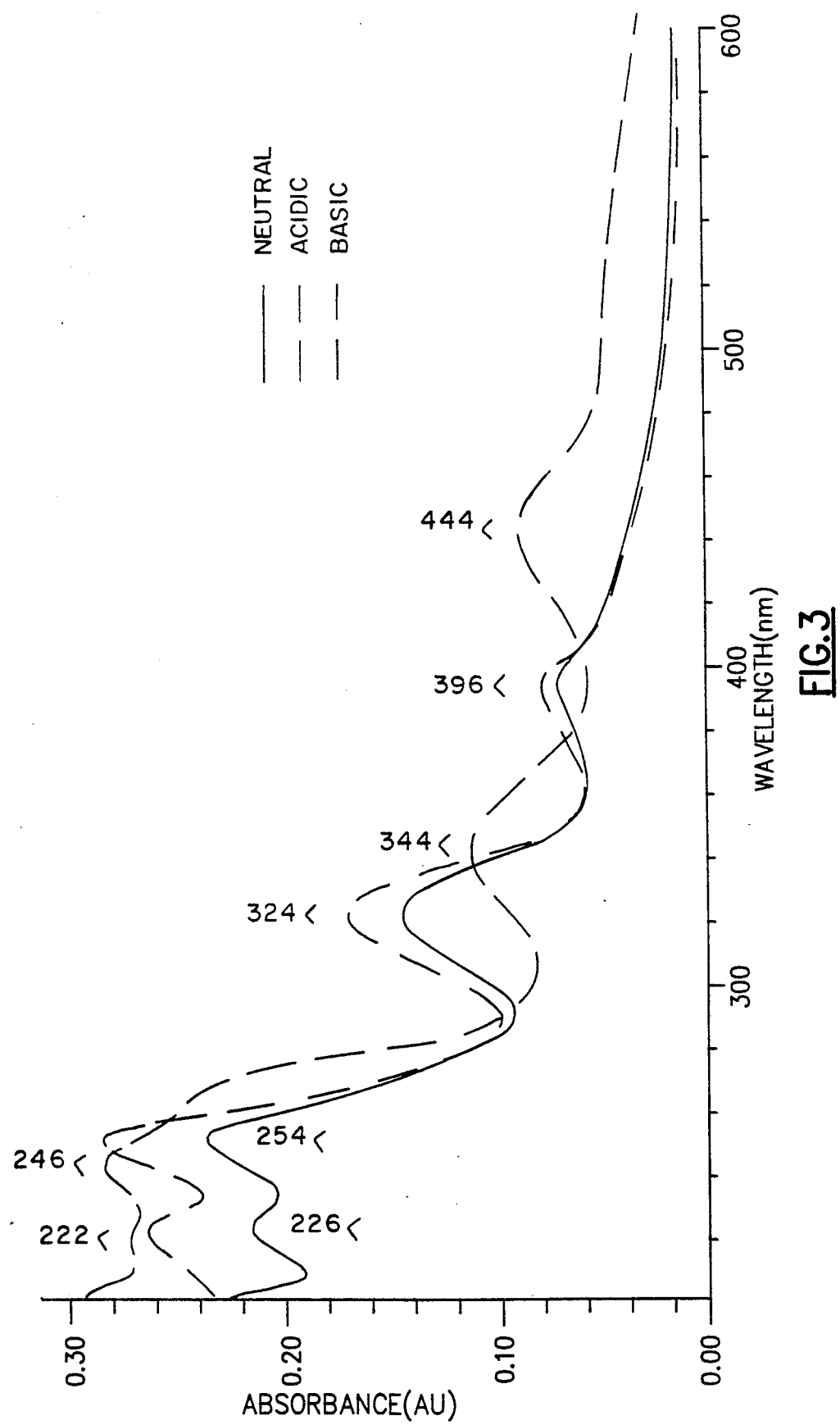
FIG. 3 is an UV spectrum of BMY-42428 in methanol.
Figure 4:
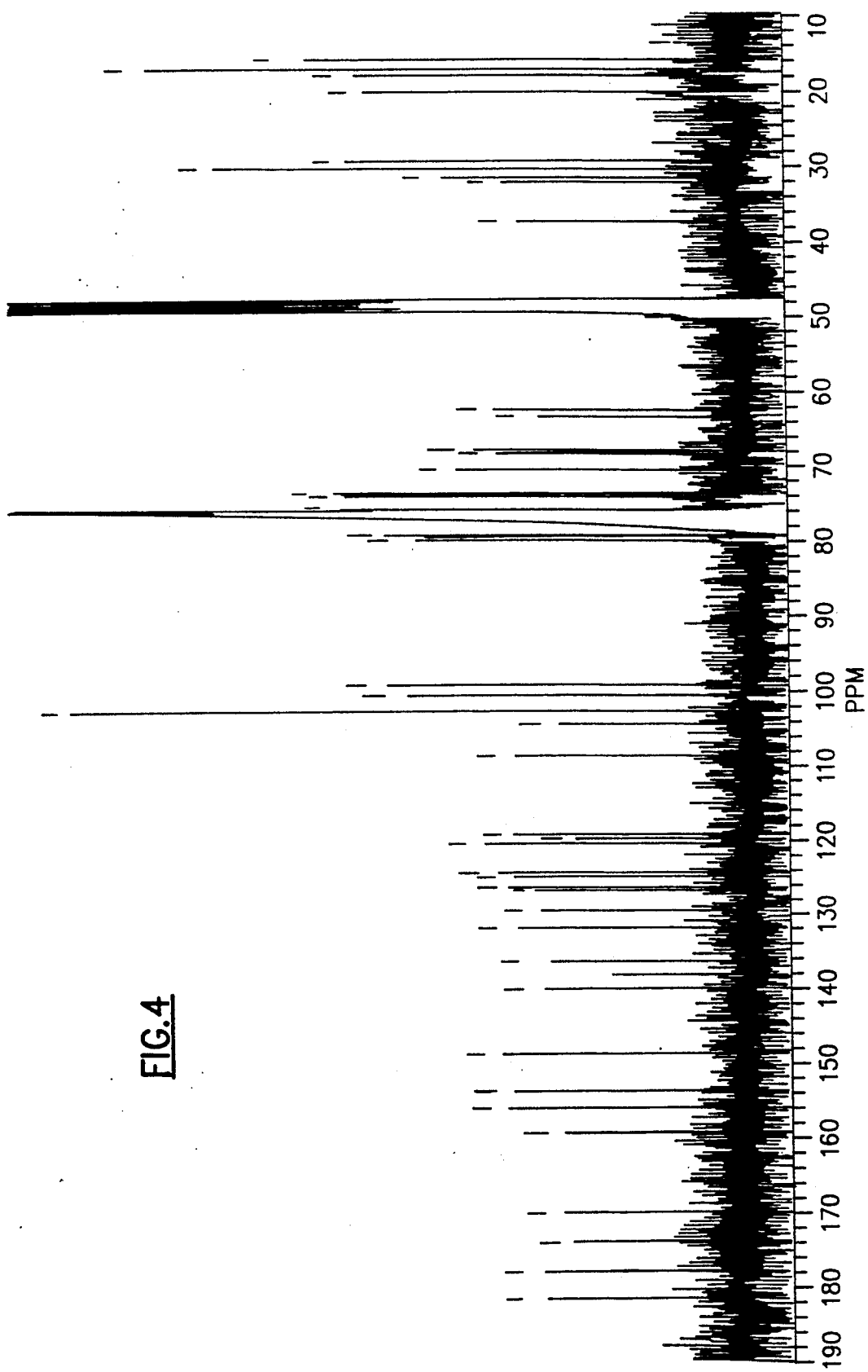
FIG. 4 is an $^{13}$C-NMR spectrum of BMY-42428 in CDCl$_3$/methanol-d$_4$.

The BMY-42428 antibiotic of the present invention may be produced by fermentation of a BMY-42428-producing strain of *Actinomadura madurae*.

The preferred producing organism is an actinomycete isolated from a soil sample collected i Athens, Greece and designated Strain Q473-8. A biologically pure culture of strain Q473-8 has been deposited with the American Type Culture Collection, Rockville, Md., and added to its permanent collection of microorganisms as ATCC-53806.

The following description of Strain Q473-8 includes cultural, physico-chemical and micromorphological observations made according to standard taxonomic procedures (1), (2).

Strain Q473-8 grows poorly on most media. Aerial mycelium is not formed, and a slight to dark brown pigment is evident i most media. Cultural characteristics are summarized in Table 1. The non-fragmenting substrate mycelium is long, 0.5-0.9 μm wide, and branched.

TABLE 1

Cultural Characteristics of Strain Q473-8

| | | |
|---|---|---|
| Yeast-Extract-Malt-Extract Agar ISP #2 | G | poor |
| | VM | colorless |
| | AM | None |
| | DP | dark yellowish brown (78)[a] |
| ISP #3 Oatmeal agar | G | scant |
| | VM | colorless |
| | AM | none |
| | DP | none |
| ISP #4 Inorganic salts-starch agar | G | scant |
| | VM | colorless |
| | AM | none |
| | DP | none |
| ISP #5 Glycerol-asparagine agar | G | poor |
| | VM | colorless |
| | AM | none |
| | DP | medium yellowish brown (77) |
| Peptone Iron agar | G | fair |
| | VM | colorless |
| | AM | none |
| | DP | medium yellowish brown (77) |
| ISP #7 Tyrosine agar | G | scant |
| | VM | colorless |
| | AM | none |
| | DP | dark yellowish brown (78) |
| Glucose-asparagine agar | G | poor |
| | VM | medium yellowish brown (77) |
| | AM | none |
| | DP | grayish yellowish brown (80) |
| Czapek's Sucrose-nitrate agar | G | poor |
| | VM | brownish pink |
| | AM | none |
| | DP | slight, grayish brown |
| Nutrient agar | G | scant |
| | VM | colorless |
| | AM | none |
| | DP | slight, grayish brown |
| Modified Bennett's agar | G | fair, moist |
| | VM | grayish brown (61) |
| | AM | none |
| | DP | grayish brown (61) |
| Thin-Potato-Carrot agar | G | none |
| ATCC Medium #5 | G | moderate, moist |
| | VM | brownish black (65) |
| | AM | none |
| | DP | brownish black (65) |
| ATCC Medium #172 | G | fair, moist |
| | VM | dark grayish brown (62) |
| | AM | none |
| | DP | brownish gray (64) |
| Potato Dextrose agar | G | scant |
| | VM | dark yellowish brown (78) |
| | AM | none |
| | DP | grayish brown (61) |
| Maltose-Tryptone agar | G | poor |
| | VM | medium yellowish brown (77) |
| | AM | none |
| | DP | gray yellowish brown (80) |
| Tomato juice agar | G | fair |
| | VM | dark orangish yellow (72) |
| | AM | none |
| | DP | deep brown (56) |
| Tryptic soy agar | G | poor |
| | VM | colorless |
| | AM | none |
| | DP | medium yellowish brown (77) |
| Xanthine agar | G | none |

[a]Color names and numbers from ISCC-NBS Color Name Charts, NBS Special Publication 440 (3)
G: Growth, VM: Vegetative Mycelium, AM: Aerial Mycelium, DP: Diffusible pigment Strain Q473-8 grows at temperatures ranging from 16°-41° C. and tolerates NaCl concentrations of 1% to 4%. Scant growth is present at a NaCl concentration of 5%. Glucose, mannitol, xylose, L-arabinose, cellobiose, rhammose, ribose and Japanese potato starch (Akadama Dextrin No. 3; Nichiden Kagaku KK) are utilized for growth. Utilization of salicin and trehalose are doubtful. Physiological properties and carbon utilization data are shown in Tables 2 and 3, respectively.

TABLE 2

Physiological Properties of Strain Q473-8

| | |
|---|---|
| Growth temperature range | 16° C. to 41° C. |
| NaCl tolerance | 1% to 4% |
| Starch hydrolysis | + |
| Gelatin liquefaction | (+) |
| Milk peptonization | + |
| Nitrate reduction | + |
| Enzymatic activity[a] | |
| Alkaline Phosphatase | +++ |
| Esterase | + |
| Esterase-Lipase | + |
| Lipase | ± |
| Leucine amino-peptidase | +++ |
| Valine amino-peptidase | ± |
| Chymotrypsin | ± |
| Acid-phosphatase | ++ |
| Phosphohydrolase | ++ |
| β-glucosidase | +++ |

[a]API ZYM method
Negative results not included.

TABLE 3

Carbon Utilization Pattern of Strain Q473-8

| | |
|---|---|
| Positive Utilization | Glucose |
| | Mannitol |
| | Xylose |
| | L-arabinose |
| | Cellobiose |
| | Rhamnose |
| | Ribose |
| | Japanese potato starch |
| Doubtful Utilization | Salicin |
| | Trehalose |
| Negative Utilization | Mannose |
| | Fructose |
| | Galactose |
| | Lactose |
| | Raffinose |
| | Sucrose |
| | Maltose |
| | D-Arabinose |
| | Sucrose |
| | Melezitose |
| | Glycerol |
| | Melibiose |
| | Dulcitol |
| | Cellulose |
| | Inositol |

Analysis of whole cell hydrolyzates reveals the presence of meso-diaminopimelic acid, ribose and madurose; hence, the organism has a type IIIB cell wall. Phospholipid analysis reveals the presence of unidentified glucosamine-containing phospholipids and traces of phosphatidyl inositol, indicating a P-IV phospholipid pattern.

The chemotaxonomic data, together with the morphological features of strain Q473-8, indicate that the organism is a member of the genus *Actinomadura*, most closely resembling *Actinomadura madurae* in its morphology and carbon utilization characteristics (4). Further characterization including menaquinone analysis is needed to determine whether strain Q473-8 has properties consistent with a recently proposed new genus, Nonomuria (5).

TABLE 4

Comparison of Strain Q473-8 with Actinomadura madurae

| Growth on | Strain Q473-8 | Actinomadura madurae[a] |
|---|---|---|
| L-arabinose | + | V |
| D-fructose | − | V |
| D-glucose | + | + |
| Glycerol | − | V |
| i-Inositol | − | − |
| D-Mannitol | + | + |
| Melibiose | − | NT |
| Raffinose | − | − |
| Rhamnose | + | V |
| Sucrose | − | − |
| D-Xylose | + | + |
| Hydrolysis of Starch | + | + |
| Nitrate reduction | + | + |
| Gelatin Liquefaction | (+) | + to (+) |
| Spore chain | absent | absent or hooks |

[a]Williams and Wellington (1981)

References Cited

1. Lechevalier et al., Society for Industrial Microbiology special publication number 6, (A. Dietz and D.W. Thayer, eds.). pages 225-291, 1980.

2. Shirling et al., Int. J. Syst. Bacteriol., vol. 16 (3):313-340, July 1966.

3. Kelly et al., ISCC-NBS color-name charts illustrated with Centroid colors. U.S. Dept. of Comm. Circ. 553, Washington, D.C., November, 1975.

4. Williams et al., "The Prokaryotes, Volume II", pages 2,103-2,117, 1981. (Eds. Starr, Stolp, Truper, Balows, Schlegel).

5. Goodfellow et al., Biology of Actinomycetes '88, (Eds. Okami, Beppu, and Ogawara) pages 233-238, 1988.

It is to be understood that the present invention is not limited to use of the particular preferred strain described above or to organisms fully answering its description. It is especially intended to include other BMY-42428-producing variants or mutants of the described organism which can be produced by conventional means such as x-radiation, ultraviolet radiation, treatment with nitrogen mustards, phage exposure, and the like.

Antibiotic Production

BMY-42428 may be produced by cultivating a BMY-42428-producing strain of *Actinomadura madurae*. preferably *Actinomadura madurae* ATCC-53806 or a mutant or variant thereof, under submerged aerobic conditions in an aqueous nutrient medium. The organism is grown in a nutrient medium containing an assimilable carbon source, for example, sucrose, lactose, glucose, rhamnose, fructose, mannose, melibiose, glycerol or soluble starch. The nutrient medium should also contain an assimilable nitrogen source such as fish meal, peptone, soybean flour, peanut meal, cottonseed meal, corn steep liquor, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired, or they may be supplied as impurities of other constituents of the media.

Production of BMY-42428 can be effected at any temperature conducive to satisfactory growth of the producing organism, e.g. 16°-41° C., but it is preferable to conduct the fermentation at 25°-35° C., most preferably 27°-32° C. A neutral pH is preferably employed in the medium and production of the antibiotic is carried out generally for a period of about five to ten days.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of BMY-42428. The medium in which the vegetative inoculum is produced can be the same as, or different from, that utilized in the tank as long as it is such that a good growth of the producing organism is obtained. Agitation during the fermentation can be provided by a mechanical impeller and conventional antifoam agents such as lard oil or silicon oil can be added if needed.

Production of BMY-42428 in the fermentation medium can be readily followed during the course of the fermentation by thin layer chromatography or HPLC with a diode assay detector such as the Hewlett-Packard HP-1040.

Isolation of the BMY-42428 antibiotic from the fermentation medium and purification of BMY-42428 may be achieved by conventional solvent extraction and chromatographic techniques. A preferred isolation and purification procedure is illustrated in Example 3 below.

The following preferred specific embodiments are intended to be merely illustrative and not to limit the scope of the invention. Unless otherwise indicated all solvent ratios are volume/volume.

EXAMPLE 1

Fermentation of BMY-42428 in Shake Flask

*Actinomadura madurae* ATCC-53806 was maintained and transferred in test tubes on agar slants of yeast-malt extract agar supplemented with calcium carbonate. This medium consisted of 4.0 g of dextrose, 2.0 g of yeast extract, 20 g malt extract, 1.5 g calcium carbonate and 20 g agar made up to one liter with distilled water. With each transfer the agar slant was incubated for 5 to 7 days at 28° C. To prepare an inoculum for the production phase, the surface growth from the slant culture was transferred to a 500 ml Erlenmeyer flask containing 100 ml of a vegetative medium consisting of 2% glucose, 1% fishmeal and 0.5% calcium carbonate. The vegetative medium was incubated for 3 days at 28° C. on a rotary shaker set at 250 rev./min. Five mls of this vegetative growth were transferred to a 500 ml Erlenmeyer flask containing 100 ml of production medium having the same composition as the vegetative medium described above. The production medium was again incubated at 28° C. on a rotary shaker set a 250 rev/min. Optimal production was generally reached at 5-6 days.

EXAMPLE 2

Fermentation of BMY-42428 in Laboratory Fermentors 100 mls of vegetative culture was prepared as described in Example 1. Twenty-five ml of this vegetative stage were transferred to a 2 liter Vitro bottle containing 500 ml of the vegetative medium. This vegetative medium was again incubated at 28° C. for 72 hours on a rotary shaker set at 250 rev/min. The vegetative medium seeded with the producing organism was used to inoculate a 16 liters nominal volume New Brunswick Microgen fermentor containing 10 liters of production medium having the same composition as the vegetative medium. An antifoam agent (polypropylene glycol 2,000; Dow Chemical, 10 ml per fermentor) was included to control foaming. The organism was allowed to grow under the following conditions: agitation, 250 rpm; temperature, 28° C., aeration 10 liters/min. BMY-42428 reached maximum production at 5-6 days.

For fermentation in a 50 liters nominal volume Biolafitte fermentor, 100 mls vegetative culture was prepared as described in Example 1. Sixteen mls each of this vegetative culture were transferred to several 2 liter Erlenmeyer flasks containing 400 ml of the same vegetative medium. These second vegetative cultures were incubated at 28° C. for 3 days on a rotary shaker set at 250 rev/min. 1,200 ml of this vegetative culture were combined and transferred to a 4 liter Vitro bottle and then inoculated into a 50 liters nominal volume Biolofitte fermentor containing 30 liters of the production medium having the same composition as the vegetative medium. The organism was allowed to grow under the following conditions' agitation 250 rpm; temperature, 28° C.; aeration, 30 liters/min. An antifoam agent (polypropylene glycol 2,000, Dow Chemical) was used to control foaming. BMY-42428 reached maximum production at about 5-6 days.

EXAMPLE 3

Isolation and Purification of BMY-42428

A flowchart summarizing the steps of this example appears below:

```
                    Fermentation Medium
                           |
                         30L
                         whole broth
              filtrate   extract with CHCl3/MeOH (2:1)
                 |              |
            aqueous         organic
                                |
            ┌───────┐        evaporate         mycelia
         aqueous    A                          discard
         discard    |dissolve in MeOH
                SOLN    PPT
                 ┌───────┴──────┐
                              B
                    |Dicalite Chromatography|
              ┌─────┬─────┬─────┬─────┐
                              |CHCl3|
                                 C
                    |Vacuum liquid
                    |chromatography
              ┌─────┬─────┬─────┬─────┐
                          5%
                       MeOH/CHCl3
                              D
                           |PTLC
                           |20% methanol/chloroform
                          BMY-42428
```

The thin layer chromatography (TLC) and analytical HPLC procedures used in the procedure below were carried out as follows:

Thin Layer Chromatography

Analytical TLC was carried out on precoated Merck Silica gel 60 F-254 plates (2.5 cm×10 cm, 0.25 mm thickness). The plates were developed in glass cylinders (6.4 cm [o.d] 11.5 cm high) purchased from Whatman, Inc. The tanks were lined with filter paper (Whatman #4), charged with 10 ml of 2 parts methanol, 8 parts chloroform and allowed to equilibrate prior to introducing the plate. The developed, air-dried plates were either visualized with 254 nm and 366 nm ultraviolet light using the Chromato-Vue model CC-20 light box (Ultra-Violet Products, Inc.) or viewed in visible light without any spray reagents, or visualized by spraying with vanillin/$H_2SO_4$ spray reagent.

Preparative TLC was performed on Merck silica gel 60 F-254 plates (20 cm×20 cm×1 mm thickness). The plates were developed in a rectangular glass tank (23 cm×22 cm×10 cm) made by Desaga, Heidelberg. The tank was lined with filter paper (Whatman #4), charged with 100 ml of 2 parts methanol, 8 parts chloroform, and allowed to equilibrate before inserting the plate. The position of the bands were delineated under UV light using the Chromato-Vue model CC-20 light box, after the developed plates have been air-dried.

Analytical HPLC

An analytical HPLC system was constructed from the following components. Waters Associates Model 6000A Solvent Delivery System pump; Waters Associates Model 440 UV/Visible Absorbance Detector set at 254 nm; Cole-Palmer Model 8373-10 Recorder; Waters Associates Model U6K Injector; Partisil 10 ODS-3 (10μ) column (4.6 mm id×25 cm). The components were connected with 316 stainless steel tubing (1.6 mm [o.d.]−0.23 mm [i.d.]). The eluant consisting of 4 parts 0.1M ammonium acetate, 5 parts tetrahydrofuran and 1 part methanol was pumped at a flow rate of 1 ml/min for all analysis.

A. Preparation of Crude Extract A

Fermentation broth (30L) obtained according to the general procedure of Example 2 was mixed with an equal volume of chloroform/methanol (2:1) solvent mixture (30L) in a polypropylene tank and stirred for 1 hour using an air-driven mixer. Four large scoops of Dicalite (diatomaceous earth; approximately 2 kg) were mixed into the suspension. The resulting mixture was filtered using a centerslung basket centrifuge. The filtrate was allowed to develop two immiscible phases which were subsequently separated. The organic chloroform layer was concentrated in vacuo in a rotary evaporator to yield 34.1 g of reddish-brown gum A.

B. Preparation of Residue B

The reddish brown gum A (34.1 g) was suspended in 300 ml of methanol and then stirred at room temperature for 30 minutes. The insoluble material was filtered off to give 3.4 g of residue B.

C. Dicalite Chromatography of Residue B

A slurry of residue B (3.4 g), 100 ml of chloroform/methanol (2:1) solvent mixture and Dicalite (10 g) was prepared in a 500 ml round bottom flask. After thorough mixing, the slurry was evaporated to dryness in vacuo in a rotary evaporator. The resulting residue was added to a flask chromatography column (4.1 cm [i.d]×46 cm), prepacked with 10 g of Dicalite. Elution commenced with pressurized flow (nitrogen, 3 psi) using the following elutropic series; 500 ml of hexanes, 500 ml of toluene, 500 ml of ether, 500 ml of ethyl acetate, 1 liter of chloroform, 1 liter acetonitrile and 500 ml of methanol. The chloroform eluant was concentrated to dryness in vacuo in a rotatory evaporator to give 712 mg of residue C.

D. Vacuum Liquid Chromatography of Residue C

A sintered glass Buchner filter funnel with a fitted disk was dry packed to a height of 4 cm with TLC grade silica gel (siliga gel 60, E. Merck). The absorbent was allowed to settle by gentle tapping under gravity followed by the application of vacuum to give a uniform and tightly packed hard cake. Vacuum was released and chloroform (30 ml) was applied to the surface of the absorbent. The vacuum was again applied and the column sucked dry.

Residue C (712 mg) was preabsorbed on a small amount of the silica gel and uniformly applied to the top of the column. Elution commenced under gentle vacuum with the following elutropic series; chloroform (100 ml), 2% methanol in chloroform (100 ml), 3% methanol in chloroform (100 ml), 5% methanol in chloroform (500 ml), 10% methanol in chloroform (700 ml) and 20% methanol in chloroform (100 ml). The 5% methanol in chloroform fraction was shown by TLC analysis to be highly enriched in two yellow spots at $R_f$ 0.30 and 0.52 (silica gel/methanol/chloroform [1:4]. Concentration in vacuo of the 5% methanol in chloroform eluant yielded residue D (247 mg).

E. Preparative Thin Layer Chromatography of Residue D

A portion of residue D (120 mg) was dissolved in 3 ml of a chloroform/methanol (1:1) solvent mixture. This solution was uniformly applied as a thin line to three preparative silica gel plates (20 cm×20 cm×1 mm thickness, E. Merck) using a TLC Plate Streaker (Kontes, catalog no. K-416430). The plates were then developed in a chamber containing methanol/chloroform (1:4). After development and drying of the plates, the band centered at $R_f$ 0.26, which could be observed in visible light and under UV light, was scraped and eluted with 15% methanol in chloroform solvent mixture. Evaporation of the eluant yielded a residue which was crystallized from chloroform/methanol/hexane to give BMY-42428 as a greenish-orange solid.

Physico-chemical Properties of BMY-42428

| Physico-chemical Properties of BMY-42428 | | |
|---|---|---|
| Description: | greenish-orange solid (crystallized from methanol/chloroform/hexane) | |
| Molecular formula: | $C_{52}H_{69}NO_{23}$ (tentative) | |
| Molecular weight: | 1075 (tentative) | |
| Ultraviolet spectrum: | Hewlett-Packard 8452A Diode Array Spectrophotometer Concentration: $9.06 \times 10^{-4}$ g/100 ml Solvent: methanol | |
| | λmax (nm) | $E_1^{1\%}$ cm |
| Neutral methanol | 226 | 239 |
| | 254 | 262 |
| | 324 | 157 |
| | 396 | 76 |
| Acidic methanol | 224 | 292 |
| | 254 | 317 |
| | 324 | 187 |
| | 396 | 85 |
| Basic methanol | 222 | 302 |
| | 246 | 315 |
| | 344 | 120 |
| | 444 | 95 |
| Infrared spectrum: | Perkin Elmer FTIR Model 1800 | |

Physico-chemical Properties of BMY-42428

Spectrometer, KBr pellet

Major IR bands: 3440, 2976, 2935, 2876, 1695, 1666, 1616, 1471, 1414, 1384, 1366, 1326, 1284, 1219, 1164, 1134, 1059, 987, 906, 890, 860, 582, 558 cm$^{-1}$.

$^1$H-NMR spectrum: Bruker Model AM-300 spectrometer, dual carbon-proton probe, 5 mm. Solvent: $d_6$-DMSO.

Observed chemical shifts (ppm): 10.35 (br, s, 1H); 8.39 (d, 1H); 8.22 (d, 1H); 7.75 (d, 1H); 7.42 (br, s, 1H); 7.36 (d, 1H); 4.94 (m, 1H); 4.80 (m, 2H); 4.66 (m, 1H); 4.47 (m, 2H); 4.38 (d, 1H), 4.17 (br, s, 1H); 3.79 (m, 2H); 3.46 (m, masked by H$_2$O); 3.09 (m, 6H); 2.33 (m, 1H); 2.01 (m, 6H); 1.89 (br, s, 8H); 1.75 (m, 4H); 1.47 (d, 6H); 1.40 (d, 3H); 1.20 (d, 6H); 1.12 (d, 9H); 1.05 (d, 3H).

$^{13}$C-NMR Spectrum: Bruker Model AM-300 spectrometer Solvent: CDCl$_3$/MeOD (4:1).

Observed chemical shifts (ppm): 186.6 (s); 177.9 (s,); 173.9 (s); 170.1 (s,); 159.3 (s); 156.1 (s); 153.8 (s); 148.6 (s); 140.2 (s); 138.2 (s); 136.3 (s); 131.7 (s); 129.5 (s); 126.7 (d); 126.3 (s); 124.8 (d); 124.3 (d); 120.3 (d); 119.6 (s); 119.3 (s); 108.7 (d); 104.4 (s); 102.8 (d); 102.7 (d); 100.8 (d); 99.1 (d); 80.0 (d); 79.7 (d); 79.5 (d); 77.4 (s); 77.2 (d); 76.5 (d); 76.0 (d); 74.5 (d); 74.3 (d); 74.2 (d); 70.5 (d); 68.3 (d); 67.9 (d); 63.2 (d); 62.4 (d); 49.4 (d); 37.4 (t); 32.3 (d); 31.7 (t); 30.5 (t); 29.6 (t); 20.3 (q); 18.3 (q); 17.93 (q); 17.89 (q); 17.8 (q); 16.3 (q).

| Analytical Thin Layer Chromatography: | |
|---|---|
| Solvent System | Rf |
| CHCl$_3$/MeOH (4:1) | 0.30 |
| Analytical HPLC: | |
| Mobile Phase | Retention Time |
| 0.1M NH$_4$OAc (4) Tetrahydrofuran (THF) (5) MeOH (1) | 5.5 minutes |

Biological Activity

BMY-42428 has been found to exhibit antimicrobial activity in standard in vitro screening tests. For example, BMY-42428 exhibits an MIC (Minimum Inhibitory Concentration) of 0.03 vs. *E. faecalis* strain A20688, 0.004 vs. *E. faecalis*/ATCC 29212, 0.016 vs. *E. faecalis*/ATCC 33186, 0.008 vs *S. aureus* strain A9537, 0.008 vs. *S. aureus*/NCCLS strain, 0.008 vs *S. aureus*/ATCC 29213, and 0.002 vs. *B. subtilis*/ATCC 6633.

BMY-42428 also exhibits antitumor activity when tested in conventional in vitro systems and in in vivo experimental animal tumor systems.

A more detailed disclosure of the antitumor testing of BMY-42428 is provided below.

BMY-42428 was tested for in vitro cytotoxic activity against a murine and a human tumor cell line. In vivo it was tested for activity against a murine leukemia tumor model.

B16-F10 (murine melanoma) and HCT-116 (human colon cancer cell lone) cells were cultured in Complete McCoys Media. The media consists of 420 ml McCoys 5A media plus 500 mg sodium bicarbonate in 6 ml water, 6.56 mg L-serine, 1.5 mg L-asparagine and 82.4 mg sodium pyruvate in 2 ml water, 6.25 ml essential amino acids (50X, Gibco), 3.0 ml non-essential amino acids (100X, Gibco), 3 ml L-glutamine (200 MM), 3 ml MEM vitamins (Gibco), 6.25 ml penicillin/streptomycin (Gibco) and 50 ml of heat-inactivated defined fetal calf serum.

The two cell lines are harvested during logarithmic phase cell growth and 3,600 cells in 150 microliter media were placed in each well of a 96 well microtiter plate. After 24 hours incubation at 37 degrees Celsius in a 95% air/5% carbon dioxide humidified incubator to allow the cells to attach to the plate, fifty microliters of sample/reference drug is added to 11 of 12 of the top row of wells while 50 microliters of media is added to the 12th. The drugs/media are serially diluted (4 fold dilutions) down the 8 wells of the plate. The cells in the presence of drug/media are then incubated for 72 hours. After fixing with 10% formalin, cells killed by the drug were washed off the plate while those surviving cells are stained with 0.0075% crystal violet. After drying, the stain is solubilized with 10% ethanol and 1% acetic acid, the developed plate quantitated on a Dynatech MR 600 plate reader and the IC50 values (drug concentration at which 50% cell death or growth inhibition occurs) calculated. The table below shows the data determined for BMY-42428.

| In Vitro Antitumor Activity (IC$_{50}$ in µg/ml) | | |
|---|---|---|
| Drug | B16-F10 | HCT-116 |
| BMY-42428 | 65536 | 262144 |

In vivo activity of BMY-42428 was determined in a murine leukemia tumor system. Female CDF1 mice were intraperitoneally inoculated with 0.5 ml of diluted ascitic fluid containing 10$^6$ lymphocytic leukemia P388 cells. Ten mice were untreated and the median survival time of this group was 10.5 days. Seven groups of 4 mice each were treated with BMY-42428 on days 1, 2, 3, 4 and 5 post tumor implant. The drug was administered ip after being initially dissolved in DMSO, Tween 80 and buffered saline. Groups treated with 9, 3 and 1 mg/kg/day suffered drug-induced toxicity and all mice died prior to day 7. Groups receiving 0.1 and 0.123 mg/kg/day had a median survival time of 14.5 days. Thus the % T/C (survival time of drug treated/survival time of untreated controls ×100) was 138%. The criteria for antitumor activity in this murine tumor test is a % T/C of 125 or greater. Thus, BMY-42428 fulfilled the criteria for antitumor activity in the P388 murine leukemia antitumor model.

| In-vivo Antitumor Activity Against P388 Leukemia | | | |
|---|---|---|---|
| Compound | Dose* (mg/kg/day) | Median Survival Time | % T/C | Body weight change on day 4 (gms) |
| BMY-42428 | 9 | Toxic | Toxic | −2.6 |
| | 3 | Toxic | Toxic | −4.1 |
| | 1 | Toxic | Toxic | −2.7 |
| | 0.3 | 14.0 | 133 | −2.5 |
| | 0.1 | 14.5 | 138 | −1.5 |

-continued

In-vivo Antitumor Activity Against P388 Leukemia

| Compound | Dose* (mg/kg/day) | Median Survival Time | % T/C | Body weight change on day 4 (gms) |
|---|---|---|---|---|
| | 0.03 | 14.0 | 133 | 0.2 |
| | 0.123 | 14.5 | 138 | 0.6 |

*IP, Q01 D × 5; 1

Therapeutic Use

As mentioned above BMY-42428 exhibits antimicrobial activity, e.g. activity against bacteria such as *E. faecalis*, *S. aureus* and *B. subtilis*.

The present invention, therefore, provides a method for treating microbial infections susceptible to BMY-42428, which comprises administering to an animal host, e.g. a warm-blooded mammal, in need of such treatment BMY-42428 or a pharmaceutical composition thereof in an amount sufficient to treat such infections.

BMY-42428 also exhibits antitumor activity against mammalian malignant tumors.

In another aspect the present invention provides a method of treating a mammalian host affected by a malignant tumor sensitive to BMY-42428, which comprises administering to said host a tumor-inhibiting dose of BMY-42428 or a pharmaceutical composition thereof.

In yet another aspect, the present invention provides pharmaceutical compositions comprising an effective antimicrobial or tumor-inhibiting amount of BMY-42428 in combination with an inert pharmaceutically acceptable carrier or diluent. Such compositions may contain other antimicrobial or antitumor agents and may be made up in any form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antimicrobial agent the BMY-42428 or pharmaceutical composition thereof is administered so that the concentration of active ingredient is greater than the minimum inhibitory concentration for the particular organism being treated.

Optimal dosages and regimens of BMY-42428 for a given mammalian host can be readily ascertained by those skilled in the art. It will of course be appreciated that the actual dose of BMY-42428 used will vary according to the particular composition formulated, the mode of application and the particular situs, host and disease being treated. Many factors that modify the action of the drug will be taken into account including age, sex, weight, diet, time of administration, route of administration, rate of excretion, condition of the patent, drug combinations, reaction sensitivities and severity of the disease.

We claim:

1. The antibiotic compound BMY-42428 characterized by:
   (a) appearing as a greenish-orange solid when crystallized from methanol/chloroform/hexane;
   (b) an ultraviolet absorption spectrum when dissolved in methanol at a concentration of $9.06 \times 10^{-7}$ g/l of:

|  | λmax (nm) | $E_{1\ cm}^{1\%}$ |
|---|---|---|
| Neutral methanol | 226 | 239 |
|  | 254 | 262 |
|  | 324 | 157 |
|  | 396 | 76 |
| Acidic methanol | 224 | 292 |
|  | 254 | 317 |
|  | 324 | 187 |
|  | 396 | 85 |
| Basic methanol | 222 | 302 |
|  | 246 | 315 |
|  | 344 | 120 |
|  | 444 | 95; |

(c) an infrared absorption spectrum (KBr pellet) showing peaks at 3440, 2976, 2935, 2876, 1695, 1666, 1616, 1471, 1414, 1384, 1366, 1326, 1284, 1219, 1164, 1134, 1059, 987, 906, 890, 860, 582, 558 $cm^{-1}$;
   (d) a $^1$H-NMR spectrum in $d_6$-DMSO exhibiting principal signals at 10.35 (br, s, 1H), 8.39 (d, 1H); 8.22 (d, 1H); 7.75 (d, 1H); 7.42 (br,s, 1H); 7.36 (d, 1H); 4.94 (m, 1H); 4.80 (m, 2H); 4.66 (m, 1H); 4.47 (m, 2H); 4.38 (d, 1H); 4.17 (br, s, 1H); 3.79 (m, 2H); 3.46 (m, masked by H$_2$O); 3.09 (m, 6H); 2.33 (m, 1H); 2.01 (m, 6H); 1.89 (br, s, 8H); 1.75 (m, 4H); 1.47 (d, 6H); 1.40 (d, 3H); 1.20 (d, 6H); 1.12 (d, 9H); 1.05 (d, 3H);
   (e) a $^{13}$C-NMR spectrum in CDCl$_3$/MeOD (4:1) exhibiting principal signals at 186.6 (s); 177.9 (s,); 173.9 (s); 170.1 (s,); 159.3 (s); 156.1 (s); 153.8 (s); 148.6 (s); 140.2 (s); 138.2 (s); 136.3 (s); 131.7 (s); 129.5 (s); 126.7 (d); 126.3 (s); 124.8 (d); 124.3 (d); 120.3 (d); 119.6 (s); 119.3 (s); 108.7 (d); 104.4 (s); 102.8 (d); 102.7 (d); 100.8 (d); 99.1 (d); 80.0 (d); 79.7 (d); 79.5 (d); 77.4 (s); 77.2 (d); 76.5 (d); 76.0 (d); 74.5 (d); 74.3 (d); 74.2 (d); 70.5 (d); 68.3 (d); 67.9 (d); 63.2 (d); 62.4 (d); 49.4 (d); 37.4 (t); 32.3 (d); 31.7 (t); 30.5 (t); 29.6 (t); 20.3 (q); 18.3 (q); 17.93 (q); 17.89 (q); 17.8 (q); 16.3 (q);
   (f) exhibiting in silica gel thin layer chromatography an Rf value of 0.30 with the solvent system CHCl$_3$/MeOH (4:1);
   (g) exhibiting a high performance liquid chromatography retention time of 5.5 minutes with a C$_{18}$ reversed phase silica gel column and the solvent system 0.1M NH$_4$OAc:THF:MeOH (4:5:1 v/v); and
   (h) which is effective in inhibiting the growth of P388 leukemia in mice.

2. The process for the production of the antibiotic BMY-42428 as defined in claim 1 which comprises cultivating a BMY-42428-producing strain of Actinomadura in an aqueous nutrient medium containing assimilable sources of carbon and nitrogen under submerged aerobic conditions until a substantial amount of BMY-42428 is produced by said organism in said culture medium and then recovering BMY-42428 from the culture medium.

3. The process according to claim 2 wherein the producing organism is Actinomadura strain Q473-8, or a BMY-42428-producing variant or mutant thereof.

4. A biologically pure culture of the microorganism Actinomadura strain Q473-8, produces the antibiotic BMY-42428 in a recoverable quantity upon cultivation in an aqueous nutrient medium containing assimilable sources of carbon and nitrogen.

5. A method for therapeutically treating an animal host affected by a microbial infection, which comprises administering to said host an effective antimicrobial dose of BMY-42428.

6. A pharmaceutical composition comprising BMY-42428 as defined in claim 1 in combination with an inert pharmaceutically acceptable carrier or diluent.

* * * * *